United States Patent [19]

Michel et al.

[11] Patent Number: 5,411,989
[45] Date of Patent: May 2, 1995

[54] NITRIC ACID ESTERS OF CYCLOHEXANOL DERIVATIVES

[75] Inventors: Helmut Michel, Mannheim; Wolfgang Bartsch, Viernheim, both of Germany

[73] Assignee: Boehringer Mannheim, GmbH, Mannheim, Germany

[21] Appl. No.: 168,163

[22] Filed: Dec. 17, 1993

Related U.S. Application Data

[62] Division of Ser. No. 920,365, Aug. 17, 1992, abandoned.

[30] Foreign Application Priority Data

Feb. 16, 1990 [DE] Germany ............... 40 04 841.1

[51] Int. Cl.⁶ ............... A61K 31/16; C07C 309/26; C07C 233/08; C07C 233/23
[52] U.S. Cl. ............... 514/616; 514/601; 514/608; 514/625; 514/626; 514/628; 514/513; 514/519; 558/440; 560/155; 560/156; 564/80; 564/160; 564/191; 564/201; 564/210; 564/217
[58] Field of Search ............... 564/80, 160, 191, 201, 564/201, 217; 558/440; 560/155, 156; 514/513, 519, 601, 608, 616, 625, 626, 628

[56] References Cited

FOREIGN PATENT DOCUMENTS 3836021 5/1990 Germany.

*Primary Examiner*—Marianne M. Cintins
*Assistant Examiner*—Phyllis G. Spivack
*Attorney, Agent, or Firm*—Nikaido, Marmelstein, Murray & Oram

[57] ABSTRACT

The invention concerns nitric acid esters of cyclohexanol of formula I

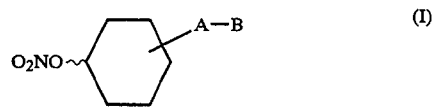

in which A signifies a valency bond or a $C_1$-$C_6$-alkylene chain and B the group —$NR^1$—CO—Z, —$NR^1$—$SO_2$—Z or —CO—$NR^2$—Z, whereby $R^1$ signifies hydrogen or a $C_1$-$C_6$-alkyl alkyl group $R^2$ hydrogen, a hydroxyl, hydroxy-$C_1$-$C_6$-alkyl, $C_1$-$C_6$-alkoxy, $C_1$-$C_6$-alkyl, $C_2$-$C_6$-alkenyl or $C_2$-$C_6$-alkynyl group and Z signifies hydrogen a $C_1$-$C_6$-alkyl, $C_2$-$C_6$-alkenyl or $C_2$-$C_6$-alkynyl group which may optionally be substituted for the case that B is an —$NR^1$—CO—Z group, Z can also signify a $C_1$-$C_6$-alkoxy group.

15 Claims, No Drawings

NITRIC ACID ESTERS OF CYCLOHEXANOL DERIVATIVES

This is a division of application Ser. No. 07/920,365 filed Aug. 17, 1992, now abandoned which is a U.S. national phase entry of International Application No. PCT/EP91/00290 filed Feb. 14, 1991.

The present invention concerns new nitric acid esters of cyclohexanol derivatives of the formula I

in which A signifies a valency bond or a $C_1$-$C_6$-alkylene chain and B the group —$NR^1$—CO—Z —$NR^1$—$SO_2$—Z or —CO—$NR^2$—Z, whereby $R^1$ signifies hydrogen or a $C_1$-$C_6$-alkyl group, $R^2$ hydrogen, a hydroxyl, hydroxy-$C_1$-$C_6$-alkyl, $C_1$-$C_6$-alkoxy, $C_1$-$C_6$-alkyl, $C_2$-$C_6$-alkenyl or $C_2$-$C_6$-alkynyl group and Z hydrogen a $C_1$-$C_6$-alkyl $C_2$-$C_6$-alkenyl or $C_2$-$C_6$-alkynyl group which can be substituted one or more times by a hydroxyl, $C_1$-$C_6$-alkylcarbonyloxy, $C_1$-$C_6$-alkoxy, halogen, cyano, carboxyl, $C_1$-$C_6$-alkoxycarbonyl, —CO—$NR^3R^4$, mercapto, $C_1$-$C_6$-alkylmercapto or $C_1$-$C_6$-alkylcarbonylmercapto group, or Z represents a $C_3$-$C_6$-cycloalkyl group or a pyridine, N-oxypyridine, tetrazolyl or pyrrolidinone ring or Z, together with $R^2$ and the nitrogen atom to which Z and $R^2$ are attached, forms a heterocyclic ring which can additionally contain an oxygen, sulphur or nitrogen atom, whereby the heterocyclic ring with an additional nitrogen atom can possibly be acylated on the nitrogen atom by a $C_1$-$C_6$-alkylcarbonyl group and, for the case that B is an —$NR^1$—CO—Z group, Z can also signify a $C_1$-$C_6$-alkoxy group, or when Z signifies $C_1$-$C_6$-alkyl or $C_2$-$C_6$-alkenyl group substituted by a mercapto, $C_1$-$C_6$-alkylmercapto or $C_1$-$C_6$-alkylcarbonyl-mercapto, the $C_1$-$C_6$-alkyl or $C_2$-$C_6$-alkenyl group can be additionally substituted by the group —$NR^4R^5$ or a $C_1$-$C_4$-alkylcarbonyl group and $R^3$ and $R^4$ can be the same or different and, in each case independently of one another, signify hydrogen, a $C_1$-$C_6$-alkyl group or $R^3$ and $R^4$, together with the nitrogen atom to which they are attached, form a heterocyclic ring which can additionally contain an oxygen, sulphur or nitrogen atom their optically-active forms and physiologically compatible salts, as well as medicaments which contain these compounds.

Similar compounds with nitroxy function are known from the earlier European Patent Applications EP-A-0,367,019 and EP-A-0,366,004. EP-A-0,367,019 describes, inter alia, nitroxycyclohexylamines which possess a terminal basic amino group. In EP-A-0,366,004 are disclosed nitroxy compounds in which the nitroxy group is attached via the group —A-B to a pyrrolidine or piperidine ring. Furthermore, in EP-A-0,359,335 are described medicaments which contain nitrate ester derivatives as active materials for the treatment of heart and circulatory diseases. There, in Examples 35–40, are disclosed cyclohexanol dinitrates which are substituted in the 2-, 3- and 4-position of the cyclohexane ring or a cyclohexanol nitrate which possesses a hydroxyl group in the 2-position.

The compounds of the general formula I according to the invention possess valuable pharmacological properties. They bring about a reduction of the oxygen requirement of the heart, an increase of the blood flow and a lowering of the blood pressure. Surprisingly, it has now been found that the claimed compounds display a nitrate-like action of especially long period of action. Therefore, they are suitable for the prophylaxis and/or treatment of heart and circulatory diseases, such as e.g. angina pectoris.

The group A-B can be attached in the 2-, 3- or 4-position of the cyclohexyl ring, whereby the 3- and 4-position is especially preferred. The group A-B can stand in the cis- or trans-position to the nitroxy group, whereby the trans-position is preferred.

The "alkyl", "alkenyl" or "alkynyl" parts in the previously mentioned groups such as e g. the alkyl, alkoxy or alkylcarbonyloxy group can in all cases, be straight-chained or branched and contain 1–6 or 2–6 carbon atoms, respectively, preferably 1–4 or 2–4 carbon atoms, respectively. Straight-chained alkyl parts are, for example, the methyl, ethyl, n-propyl, n-butyl or n-pentyl radical. Branched-chain alkyl parts are, for example, the groups —$CH(CH_3)$—, —$C(CH_3)_2$—, —$CH(CH_3)$—$CH_2$, —$C(CH_3)_2$—$CH_2$— or —$CH_2$—$CH(CH_3)$—$CH_2$—.

The "alkenyl" parts are, above all, straight-chained radicals, such as e.g. the vinyl, 1-propenyl or 2-propenyl group. The "alkynyl" parts are straight-chained or branched, for example the propargyl or 2-methyl-3-butynyl group.

In the formula I, A can signify a valency bond or a straight-chained or branched $C_1$-$C_6$-alkylene croup whereby the methylene, ethylene, methylmethylene and dimethylmethylene groups are preferred.

$R^1$ can signify hydrogen or a $C_1$-$C_6$-alkyl group, for example the methyl, ethyl, n-propyl or isopropyl group.

$R^2$ can signify hydrogen, a hydroxyl or alkoxy group of 1–6 C-atoms. The methoxy, ethoxy, n-propoxy and isopropoxy group is preferred If $R^2$ signifies a straight-chained or branched alkyl or hydroxyalkyl group Of 1–6 C-atoms, then the methyl ethyl, n-propyl, isopropyl, n-butyl, isobutyl, n-pentyl, isopentyl, n-hexyl and isohexyl group come into question. $R^2$ can also signify a straight-chained or branched $C_2$-$C_6$-alkenyl or alkynyl group. The vinyl allyl 2-methylallyl and the 2-methyl-3-butynyl group are preferred. For the case that $R^2$, together with Z, forms a ring, which can possibly be interrupted by an oxygen, sulphur or possibly acylated nitrogen atom, there come into question the aziridine, the azetidine, the pyrrolidine, the piperidine, the morpholine, the thiomorpholine and the N-acetylpiperazine ring.

Z can signify hydrogen, a straight-chained or branched $C_1$-$C_6$-alkyl group or a straight-chained or branched $C_2$-$C_6$-alkenyl or alkynyl group. These groups can be substituted one, two or three times, whereby the substituents can be the same or different. Alkyl, alkenyl or alkynyl groups, which can preferably be substituted once or twice, are especially those groups with up to 5 C-atoms, such as e.g. the methyl, ethyl, n-propyl, i-propyl, 2-methyl-2-propyl, t-butyl, vinyl, propargyl or 2-methyl-3-butynyl group. The substituents of these groups mentioned in the definition of Z can stand on any desired C-atom. Preferred radicals for Z are the following: —$CH_2$—, —$CH(CH_3)$—, —$C(CH_3)_2$—, —$CH_2$—$CH_2$—, —$CH(CH_3)$—$CH_2$—, —$C(CH_3)_2$—$CH_2$—, —$CH_2$—$CH_2$—$CH_2$—, —$CH_2$—$CH(CH_3)$—$CH_2$— and —CH=CH—. As substituents of these radicals, the following especially come into question: a halogen atom, such as e.g. a chlorine or bromine atom, a carboxyl, —$R^3R^4N$—CO—, $C_1$–$C_6$-alkoxy, such as e.g. methoxy or ethoxy; $C_1$–$C_6$-alkylcarbonyloxy, such as e.g. methylcarbonyloxy; hydroxyl; cyano or $C_1$–$C_6$-alkylcarbonylmercapto group, whereby $R^3$ and $R^4$ can be the same or different and represent a hydrogen atom or a $C_1$–$C_6$-alkyl group. Preferred radicals which carry two substituents are $C_1$–$C_6$-alkyl groups, especially the —C(CH₃)(CH₂—)(CH₂—)— radical, whereby, as substituents, the hydroxyl or alkylcarbonyloxy group preferably come into question. The groups —C(CH₃)(CH₂OH)₂ and —C(CH₃)(CH₂—O—CO—CH₃)₂ are especially mentioned.

Z is preferably the methyl, ethyl, n-propyl, isopropyl, n-butyl, tert.-butyl, vinyl, allyl, 2-methylallyl, the hydroxymethyl, acetoxymethyl, methoxymethyl, ethoxymethyl, isopropoxymethyl, bromomethyl, chloromethyl or the cyanomethyl group, as well as the 1-(hydroxy-)-ethyl, 1-(acetoxy)-ethyl, 1-(methoxy)ethyl, 1-(isopropyl)-ethyl, the mercaptomethyl, methylmercaptomethyl, acetylmercaptomethyl, 1-mercaptoethyl, 1-(methylmercapto)-ethyl, 1-(acetylmercapto)-ethyl, 2-mercaptoethyl, 2-(methylmercapto)-ethyl, 2-(acetylmercapto)-ethyl, 1-ethoxycarbonyl-2-mercaptoethyl, 1-ethoxycarbonyl-2-methylmercaptoethyl, 1-ethoxycarbonyl-2-acetylmercaptoethyl, 1-ethoxycarbonyl-3mercaptopropyl, 1-ethoxycarbonyl-3-methylmercaptopropyl, 1-ethoxycarbonyl-3-acetylmercaptopropyl group as well as the 2-(hydroxy)-ethyl, 3-(hydroxy)-propyl or the 1,1-dimethyl-2-hydroxyethyl group.

Furthermore, for Z there come into question the hydroxycarbonylmethyl, 1-(hydroxycarbonyl)-ethyl, 2-(hydroxycarbonyl)-ethyl, 3-(hydroxycarbonyl)-propyl, 2-(hydroxycarbonyl)-propyl, 2-(hydroxycarbonyl)-vinyl, methoxycarbonylmethyl, ethoxycarbonylmethyl, 1-(methoxycarbonyl)-ethyl, 1-(ethoxycarbonyl)-ethyl, 2-(methoxycarbonyl)-ethyl, 2-(ethoxycarbonyl)-ethyl, 3-(methoxycarbonyl)-propyl, 3-(ethoxycarbonyl)-propyl, 2-(methoxycarbonyl)-propyl, 2-(ethoxycarbonyl)-propyl, 2-(methoxycarbonyl)-vinyl, 2-(ethoxycarbonyl)-vinyl, aminocarbonylmethyl, 1-(aminocarbonyl)-ethyl, 2-(aminocarbonyl)-ethyl, 2-(aminocarbonyl)-propyl, 3-(aminocarbonyl)-propyl, 2-(aminocarbonyl)-vinyl, methylaminocarbonylmethyl, 1-(methylaminocarbonyl)ethyl, 2-(methylaminocarbonyl)-ethyl, 2-(methylaminocarbonyl)-propyl, 3-(methylaminocarbonyl)-propyl, 2-(methylaminocarbonyl)-vinyl, dimethylaminocarbonylmethyl, 1-(dimethylaminocarbonyl)-ethyl, 2-(dimethylaminocarbonyl)-ethyl, 2-(dimethylaminocarbonyl)-propyl, 3-(dimethylaminocarbonyl)-propyl, 2-(dimethylaminocarbonyl)-propyl, 3-(dimethylaminocarbonyl)-propyl, 2-(dimethylaminocarbonyl)-vinyl group.

For the case that Z is an alkyl or alkenyl group which is substituted by the group —CO—NR³R⁴ and R³ and R⁴ can form a ring which can possibly also be interrupted by an oxygen sulphur or acylated nitrogen atom, there come into question the pyrrolidinocarbonylmethyl, piperidinocarbonylmethyl, morpholinocarbonylmethyl, thiomorpholinocarbonylmethyl, the N-acetylpiperazinocarbonylmethyl, 1-(pyrrolidinocarbonyl)-ethyl, 1-(piperidinocarbonyl)-ethyl, 1-(morpholinocarbonyl)ethyl, 1-(thiomorpholinocarbonyl)-ethyl, 1-[(N-acetyl)piperazinocarbonyl]-ethyl, 2-(pyrrolidinocarbonyl)-ethyl, 2-(piperidinocarbonyl)-ethyl, 2-(morpholinocarbonyl)ethyl, 2-(thiomorpholinocarbonyl)-ethyl, 2-[(N-acetyl)piperazinocarbonyl]-ethyl, 3-(pyrrolidinocarbonyl)propyl, 3-(piperidino)-3-carbonyl)-propyl, 3-(morpholinocarbonyl)-propyl, 3-(thiomorpholinocarbonyl)-propyl, 3-[(N-acetyl)-piperazinocarbonyl]propyl, 2-(pyrrolidinocarbonyl)-propyl, 2-(piperidinocarbonyl)-propyl, 2-(morpholinocarbonyl)-propyl, 2-(thiomorpholinocarbonyl)-propyl, 2-[(N-acetyl)piperazinocarbonyl]-propyl, 2-(pyrrolidinocarbonyl)vinyl, 2-(piperidinocarbonyl)-vinyl, 2-(morpholinocarbonyl)-vinyl, 2-(thiomorpholinocarbonyl)-vinyl and the 2-[(N-acetyl)-piperazinocarbonyl]-vinyl group.

For the case that Z represents a $C_1$–$C_6$-alkyl or $C_2$–$C_6$-alkenyl group substituted by a mercapto, $C_1$–$C_6$-alkylmercapto or $C_1$–$C_6$-alkylcarbonylmercapto, this can additionally also be substituted by an amino, $C_1$–$C_3$-alkylamino or $C_1$–$C_3$-alkylcarbonylamino group. Preferred in this sense are the 1-amino-2-mercaptoethyl, 1-amino-2-methylmercaptoethyl, 1-amino-2-acetylmercaptoethyl, 1-menhylamino-2-mercaptoethyl, 1-methylamino-2-methylmercaptoethyl, 1-methylamino-2-acetylmercaptoethyl, 1-acetylamino-2-mercaptoethyl, 1-acetylaminomethylmercaptoethyl, 1-acetylamino-2-acetylmercaptoethyl, 1-amino-2-mercapto-2-methylpropyl, 2-amino-3-mercaptopropyl, 1-amino-3-methylmercaptopropyl, 1-amino-3-acetylmercaptopropyl, 1-methylamino-3-mercaptopropyl, 1-methylamino-3-methylmercaptopropyl, 1-methylamino-3-acetylmercaptopropyl, 1-acetylamino-3-mercaptopropyl, 1-acetylamino-3-methylmercaptopropyl, 1-acetylamino-3-acetylmercaptopropyl group.

For the case that Z represents a $C_3$–$C_6$-cycloalkyl radical, one understands thereunder the cyclopropyl, cyclobutyl, cyclopentyl or cyclohexyl radical.

If Z signifies a pyridyl radical or its N-oxide, the linkage can be in the 2-, 3- or 4-position. If Z signifies a tetrazol-5-yl radical, then B is especially the group —CO—NR²—Z.

For the case that $R^3$ and $R^4$ or Z and $R^2$ together form a heterocyclic ring with a nitrogen atom, which can additionally contain an oxygen, sulphur or nitrogen atom, then one understands thereunder especially a pyrrolidine, piperidine, morpholine, thiomorpholine or piperazine ring or their N-cyclised derivatives, such as e.g. N-$C_1$–$C_6$-alkylcarbonyl derivatives.

The following meanings for A and B in formula I preferably come into question:

A signifies a valency bond or a $C_1$–$C_3$-alkylene group especially the —CH₂— group.

B signifies the groups —NR¹—CO—Z—, —NR¹—SO₂—Z or —CO—NR²—Z, whereby R¹ represents a hydrogen atom or a $C_1$–$C_3$-alkyl group, especially the methyl or ethyl group, and R² represents a hydrogen atom, a hydroxyl, hydroxy-$C_1$–$C_3$-alkyl or $C_1$–$C_3$-alkyl group, especially the methyl or ethyl group, or R² and Z together form a morpholino group R³ and R⁴, independently of one another, represent a hydrogen atom or a $C_1$–$C_3$-alkyl group, especially the methyl group, Z a hydrogen atom, a $C_1$–$C_6$-alkyl group such as e g the methyl, ethyl, tert.-butyl or n-pentyl group; a $C_2$–$C_6$-alkenyl group, such as e.g. the vinyl group; or a $C_2$–$C_6$-alkynyl group, such as e.g. —C(CH₃)₂—C≡CH—, whereby the alkyl and alkenyl groups can be substituted once by a halogen atom, such as e.g. chlorine or bromine atom; a carboxyl; carboxamido, $C_1$–$C_3$-alkoxy, $C_1$–$C_3$-alkylcarbonyloxy hydroxy or cyano group; such as e.g. the groups —CH₂Cl, —C(CH₃)₂—Br, —CH₂—COOH, —CH(CH₃)—COOH, —CH₂CH- $_2$COOH, —CH=CH—COOH, —CH$_2$—CONH$_2$, —C(CH$_3$)$_2$—CONH$_2$, —CH$_2$—CH$_2$—CONH$_2$, —CH=CH—CONH$_2$, —CH$_2$—CO—N(CH$_3$)$_2$, —CH$_2$—CH$_2$—CON(CH$_3$)$_2$, —CH$_2$—OCH$_3$, —CH—O—COCH$_3$, —CH(CH$_2$)—O—COCH$_3$, —C(CH$_3$)$_2$—CH$_2$—O—COCH$_3$, —CH$_2$OH, —CH$_2$CH$_2$OH, —CH$_2$CH$_2$CH$_2$OH, —CHOH—CH$_3$, —C(CH$_3$)$_2$—CH$_2$OH, —CH$_2$—CH(CH$_3$)—CH$_2$OH, or the alkyl and alkenyl groups can be substituted twice by hydroxyl or C$_1$-C$_3$-alkylcarbonyloxy groups, such as e.g. —C(CH$_3$)(CH$_2$OH)$_2$ or —CH(CH$_3$)(CH$_2$—O—COCH$_3$)$_2$. Furthermore Z signifies a 3- or 4-pyridyl group or N-oxypyridyl group or the pyrrolidinone ring. For the case that B signifies an —NR$^2$—CO—Z group, Z is preferably a C$_1$-C$_3$-alkoxy group, such as e.g. the ethoxy group.

Furthermore, those cyclohexanol nitrates of the formula I preferably come into question in which A signifies a valency bond or a C$_1$-C$_6$-alkylene chain and B the group —NR$^1$—CO—Z or —CO—NR$^2$—Z, whereby R$^1$ can signify hydrogen or a C$_1$-C$_6$-alkyl group, R$^2$ hydrogen, a hydroxyl, C$_1$-C$_6$-alkoxy, C$_1$-C$_6$-alkyl, or C$_2$-C$_6$-alkynyl group and Z represents a hydrogen, a C$_1$-C$_6$-alkyl or C$_2$-C$_6$-alkenyl group, which can be substituted one or more times by a hydroxyl, C$_1$-C$_6$-alkylcarbonyloxy, C$_1$-C$_6$-alkoxy, halogen, cyano, carboxyl C$_1$-C$_6$-alkoxycarbonyl or —CO—NR$^3$R$^4$ group, or Z represents a C$_3$-C$_6$-cycloalkyl group or a pyridine, N-oxypyridine, tetrazolyl or pyrrolidinone ring or Z together with R$^2$, forms a heterocyclic ring which can additionally contain an oxygen, sulphur or nitrogen atom and, for the case that B represents the group —NR$^1$—CO—Z, Z can also signify a C$_1$-C$_6$-alkoxy group, R$^3$ and R$^4$ can be the same or different and, in each case independently of one another, hydrogen, a C$_1$-C$_6$-alkyl group or R$^3$ and R$^4$ together with the nitrogen atom to which they are attached, form a heterocyclic ring which can additionally contain an oxygen sulphur or nitrogen atom, as well as their optically-active forms and physiologically compatible salts.

The following meanings are thereby preferred: A signifies a valency bond or a C$_1$-C$_3$-alkylene group R$^1$ signifies a hydrogen atom or the methyl or ethyl group R$^2$, signifies a hydrogen atom or a hydroxyl or C$_1$-C$_4$-alkyl group, R$^3$ and R$^4$ are the same or different and signify a hydro-on atom or a C$_1$-C$_3$-alkyl group or R$^3$ and R$^4$ or Z and R$^2$, together with the nitrogen atom to which they are attached, form a pyrrolidine, piperidine, morpholine, thiomorpholine or piperazine ring, as well as their N-acylated derivatives, Z signifies a hydrogen atom, a C$_1$-C$_6$-alkyl or C$_2$-C$_6$-alkenyl group which can be substituted by a hydroxyl, carboxyl, halogen, cyano or —CO—NR$^3$R$^4$ group or Z is a pyrrolidin-2-one or pyridinyl group.

The compounds of the general formula I according to the invention can be prepared in per se known manner in that one 1) subjects a compound of the general formula II

 (II)

in which A and B have the above-given meanings, to a nitrate ester formation reaction, 2) or reacts a compound of the general formula III

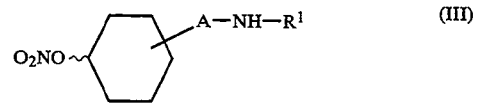 (III)

with a compound of the general formula IV,

W—CO—Z (IVa) or W—SO$^2$—Z (IVb)

whereby R$^1$ and Z have the above-given meanings and W represents a reactive group, or 3) reacts a compound of the general formula V,

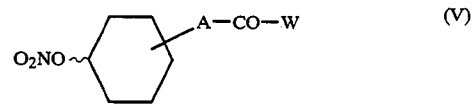 (V)

with a compound of the general formula VI,

R$^2$—NH—Z (VI)

whereby R$^2$, W, A and Z have the given meanings, and possibly converts the so-prepared compounds of the formula I into other compounds of the formula I.

Some compounds of the general formula II are new. They can be prepared in that, in per se known manner, one 1) reacts a compound of the general formula VII,

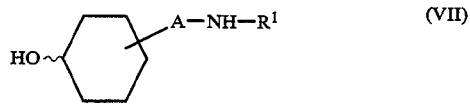 (VII)

whereby R$^1$ and A have the above-given meanings, with a compound of the general formula IV, or 2) reacts a compound of the general formula VIII

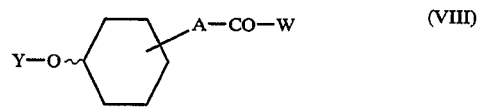 (VIII)

whereby A and W have the given meanings and Y represents a protective group, with a compound of the general formula VI and subsequently splits off the protective group Y.

The nitrate ester formation reaction for the preparation of compounds of the formula I can be carried out in that one reacts the compounds of the general formula II with a nitric acid ester-forming reagent such as fuming nitric acid, a mixture of fuming nitric acid and acetic anhydride, a mixture of fuming nitric acid and conc. sulphuric acid or dinitrogen pentoxide, at low temperatures in the presence or absence of an inert solvent.

The reaction temperatures lie between room temperature and $-60°$ C., preferably between $-30°$ C. and $0°$ C. The mole ratio of the reaction partners lies between 1 and 10.

As reactive group W, there come into question halides, such as chlorine or bromine, alkyl carboxylates or the hydroxyl group. Therefore, the correspondingly activated carboxylic acids IV and V are present in the form of esters, lactones, carboxylic acid halides or anhydrides. However, the activation of the carboxylic acids can also take place by activating reagents such as N,N-carbonyldiimidazole, N,N-dicyclohexylcarbodiimide or chloroformic acid esters. The mole ratios between the reaction partners can be chosen between 1 and 100.

As protective group Y, there come into question the usual hydroxyl protective groups, for example the acetyl group.

Compounds of the general formula VII, wherein A signifies a valency bond, $R^1$ hydrogen or acetyl, are described in Ber. 72, 995 (1939). Similar compounds can be prepared in an analogous way. If A in formula VII signifies a valency bond and $R^1$ a chloroacetyl or chloropropionyl group, then these compounds are described as intermediate products in EP-A-367,019. Other compounds of the formula VII can be prepared analogously.

Compounds of the general formula VIII wherein A signifies a valency bond, Y an acetyl proud and W a hydroxyl group can be prepared as described in J. Chem. Soc. 1950, 1379. Other compounds of the formula VIII can be prepared analogously.

The compounds III and V are known from EP-A-192,829 and are there described as intermediate products of the formulae XI and IX.

Subsequent conversions of compounds of the formula I into other compounds of the formula I takes place, for example, in that one converts a carboxyl group by reaction with alcohols into the corresponding ester derivatives or by reaction with amines into the corresponding amides. The carboxylic acids used can possibly be previously converted into the active carboxylic acid derivatives, such as e.g. anthydrides or halides, according to per se known methods. If Z represents a radical substituted by an alkylcarbonyloxy group, then such compounds can be converted by hydrolysis of this ester into the corresponding hydroxy-substituted derivatives. If Z signifies an N-oxypyridine ring, then these are preferably prepared from the corresponding pyridine derivatives of the formula I in that these are subsequently oxidised by oxygen group-transferring reagents, such as e.g. hydrogen peroxide.

The compounds of the general formula I according to the invention are cyclohexane derivatives, the substituents —$ONO_2$ and A-B of which can be in the 1,2-, 1,3- or 1,4-position. The configuration can, in each case, be cis or trans. For the case of the 1,2- or 1,3-position, the compounds according to the invention possess two chiral carbon atoms. Therefore, the subject of the invention are also all racemates, diastereomeric mixtures and optically-active forms of the compounds of the general formula I according to the invention.

The preparation of the pharmacologically compatible salts of the compounds of the formula I takes place by reaction with alkali metal or alkaline earth metal hydroxides or carbonates or with organic bases, such as e.g. triethylamine.

The substances of the general formula I and their salts can be administered enterally or parenterally in liquid and solid form. As injection medium, water is preferably used which contains the additives usual in the case of injection solutions, such as stabilising agents, solubilising agents or buffers. Such additives are e.g. tartrate or citrate buffers, ethanol, complex formers (such as ethylenediamine-tetraacetic acid or its non-toxic salts), high molecular polymers (such as liquid polyethylene oxide) for viscosity regulation. Solid carrier materials are e.g. starch, lactose, mannitol, methyl cellulose, talc, highly dispersed silica gel acids, high molecular fatty acids (such as stearic acid), gelatine, agar-agar, calcium phosphate, magnesium stearate, animal and vegetable fats and solid high molecular polymers (such as e.g. polyethylene glycols). Compositions suitable for oral administration can, if desired, contain flavouring and sweetening materials.

Medicaments containing compounds of the formula I are preferably administered orally once a day. The medicaments can contain the compounds according to the invention in an amount of 1–50 mg, preferably of 5–30 mg per form of administration.

Besides the examples set out in the following, the following compounds also, for example, come into the meaning of the present invention:

1. N-methyl-N-(trans-4-nitroxycyclohexyl)-succinic acid monoamide
2. N-methyl-N-(trans-4-nitroxycyclohexyl)-succinic acid diamide
3. N-methyl-N-(trans-4-nitroxycyclohexyl)-N',N'-dimethylsuccinic acid diamide
4. cis-N-formyl-3-nitroxycyclohexylamine
5. N-(cis-3-nitroxycyclohexyl)-succinic acid monoamide
6. N-(cis-3-nitroxycyclohexyl)-succinic acid diamide
7. N-(cis-3-nitroxycyclohexyl)-N',N'-dimethylsuccinic acid diamide
8. trans-N-formyl-2-nitroxycyclohexylamine
9. trans-N-acetyl-2-nitroxycyclohexylamine
10. N-(trans-2-nitroxycyclohexyl)-succinic acid monoamide
11. N-(trans-2-nitroxycyclohexyl)-succinic acid diamide
12. N-(trans-2-nitroxycyclohexyl)-N',N'-dimethylsuccinic acid diamide
13. 2-cyano-2-methyl-N-(trans-4-nitroxycyclohexyl)-propionic acid amide
14. cis-N-formyl-4-nitroxycyclohexylamine
15. trans-4-nitroxycyclohexanecarboxylic acid N-(tetrazol-5-yl)-amide
16. 2-methylmercapto-N-(trans-4-nitroxycyclohexyl)acetic acid amide
17. 2-amino-3-methylmercapto-N-(trans-4-nitroxycyclohexyl)-propionic acid amide
18. 2-methylamino-3-methylmercapto-N-(trans-4-nitroxycyclohexyl)-propionic acid amide
19. 2-methylamino-3-acetylmercapto-N-(trans-4-nitroxycyclohexyl)-propionic acid amide
20. 2-acetylamino-3-mercapto-N-(trans-4-nitroxycyclohexyl)-propionic acid amide
21. 2-acetylamino-3-acetylmercapto-N-(trans-4-nitroxycyclohexyl)-propionic acid amide
22. 2-amino-3-mercapto-3-methyl-(N-trans-4-nitroxycyclohexyl)-butyric acid amide
23. 2-amino-4-methylmercapto-N-(trans-4-nitroxycyclohexyl)-butyric acid amide
24. 2-acetylamino-4-methylmercapto-N-(trans-4-nitroxycyclohexyl)-butyric acid amide
25. trans-4-nitroxycyclohexane-carboxylic acid-N-[2-(3-mercapto)-propionic acid ethyl ester] amide
26. trans-4-nitroxycyclohexane-carboxylic acid N-[2-(3-acetylmercapto)-propionic acid ethyl ester] amide
27. trans-4-nitroxycyclohexane-carboxylic acid N-[2-(4-methylmercapto)-butyric acid ethyl ester] amide
28. trans-4-nitroxycyclohexane-carboxylic acid N-(2-mercaptoethyl)-amide 29. 2-mercapto-N-(trans-4-nitroxycyclohexyl)-acetic acid amide.

EXAMPLE 1 trans-N-acetyl-4-nitroxycyclohexylamine 28.3 ml (0.3 mol) acetic acid anhydride are mixed with 375 ml acetonitrile, cooled in an ice-bath to 0°–5° C. and 12.6 ml (0.3 mol) 100% nitric acid added dropwise. After 30 minutes, 15.7 g (0.1 mol) solid trans-N-acetyl-4-hydroxycyclohexylamine are added thereto with stirring and cooling at 0°–5° C. The reaction mixture is further stirred for 3 h at 0°–5° C. and subsequently allowed to flow carefully into a solution of 150 g (18 mol) sodium hydrogen carbonate in 500 ml ice water. After extraction with ethyl acetate, drying of the organic phase with sodium sulphate and distilling off in a vacuum, there remain 17.8 g of crude product. After recrystallisation from ethyl acetate, there are obtained 10.3 g of the title compound of the m.p. 146°–148° C., i.e. 50% of theory.

In analogous way are obtained:
1/1: trans-N-4-hexanoyl-4-cyclohexylamine from trans N-n-hexanoyl-4-hydroxycyclohexylamine melting point: 100°–101° C. (ether), yield: 58%
1/2: trans-4-nitroxycyclohexanecarboxylic acid amide from trans -4-hydroxycyclohexanecarboxylic acid amide melting point: 160°–159° C. (ethyl acetate), yield: 62%
1/3: trans-4-nitroxycyclohexanecarboxylic acid dimethylamide from trans-4-hydroxycyclohexanecarboxylic acid dimethylamide melting point: 108°–110° C. (ethyl acetate), yield: 40%
1/4: trans-4-nitroxycyclohexanecarboxylic acid morpholide from trans-4-hydroxycyclohexanecarboxylic acid morpholide melting point: 89°–90° C. (ether), yield: 40%
1/5: cis-N-acetyl-4-nitroxycyclohexylamine from cis-N-acetyl-4-hydroxycyclohexylamine melting point: 107°–109° C. (ether), yield: 45%
1/6: 2-chloro-N-(trans-4-nitroxycyclohexyl)-acetic acid amide from 2-chloro-N-(trans-4-hydroxycyclohexyl)-acetic acid amide melting point: 102°–104° C. (ether), yield: 34%
1/7: 2-bromo-2-methyl-N-(trans-4-nitroxycyclohexyl)propionic acid amide from 2-bromo-2-methyl-N-(trans-4-hydroxycyclohexyl)propionic acid amide melting point: 92°–94° C. (ether/isohexane), yield: 60%
1/8: N-(trans-4-nitroxycyclohexyl)-acrylic acid amide from N-(trans-4-hydroxycyclohexyl)-acrylic acid amide melting point: 160°–162° C. (ethyl acetate), yield: 63%
1/9: 2-cyano-N-(trans-4-nitroxycyclohexyl)-acetic acid amide from 2-cyano-N-(trans-4-hydroxycyclohexyl)-acetic acid amide melting point: 149°–150° C. (ether), yield: 53% of theory.

EXAMPLE 2 trans-N-acetyl-4-nitroxycyclohexylamine

A solution of 2.3 g (0.015 mol) trans-4-nitroxycyclohexylamine in 25 ml ethyl acetate is mixed with 10 ml (0.13 mol) acetic acid anhydride and stirred overnight at room temperature. One cools to 5° C., adds 100 ml of ethanol thereto and, after standing overnight at room temperature, it is distilled off in a vacuum. trituration with ether, the crystals are filtered off with suction.

There remain 1.5 g of the title compound of the m.p. 146°–148° C., i.e. 50% of theory.

Analogously, there are obtained:
2/1: trans-N-acetyl-4-nitroxycyclohexylmethylamine from trans-4-nitroxycyclohexylmethylamine melting point: 91°–93° C. (ether), yield: 30%
2/2: cis-N-acetyl-3-nitroxycyclohexylamine from cis-3-nitroxycyclohexylamine melting point: 112°–113° C. (ether), yield: 41%
2/3: trans-N-methyl-N-acetyl-4-nitroxycyclohexylamine from trans-N-methyl-4-nitroxycyclohexylamine melting point: 37°–39° C. (ether/isohexane), yield: 77% of theory
2/4: trans-N-ethyl-N-acetyl-4-nitroxycyclohexylamine from trans-N-ethyl-4-nitroxycyclohexylamine melting point: 68°–69° C. (ether), yield: 35% of theory.

EXAMPLE 3 trans-N-formyl-4-nitroxycyclohexylamine

A mixture of 6.8 ml (0.072 mol) acetic acid anhydride and 2.8 ml (0.072 mol) formic acid is heated for 2 h to 60° C. and thereafter mixed, with cooling at 5° C., with 1.9 g (0.012 mol) trans-4-nitroxycyclohexylamine. One leaves to stir overnight at room temperature, subsequently dilutes with 100 ml ethyl acetate and adds 100 ml of water thereto. After neutralisation with saturated sodium hydrogen carbonate solution, the organic phase is dried with sodium sulphate and distilled off in a vacuum. After trituration with ether, the crystals are filtered off with suction. One obtains 1.5 g of the title compound of the m p 148°–150° C., i.e. 66% of theory.

Analogously, there are obtained:
3/1: trans-N-formyl-4-nitroxycyclohexylmethylamine from trans-4-nitroxycyclohexylmethylamine melting point: oil, yield: 70%
3/2: trans-N-methyl-N-formyl-4-nitroxycyclohexylamine from trans-N-methyl-4-nitroxycyclohexylamine melting point: 52°–54° C. (ether/isohexane), yield: 60% of theory.

EXAMPLE 4

N-(trans-4-nitroxycyclohexyl)-succinic acid monoamide

To a solution of 4.8 g (0.03 mol) trans-4-nitroxycyclohexylamine in 25 ml acetonitrile one adds at 10° C. 3 g (0.03 mol) succinic acid anhydride and leaves to stir for 48 h at room temperature. After suction filtration, there remain 3.6 g of the title compound of the melting point 136°–138° C., i.e. 46% of theory.

Analogously, there are obtained:
4/1: N-(trans-4-nitroxycyclohexyl)-maleic acid monoamide from trans-4-nitroxycyclohexylamine and maleic acid anhydride melting point: 178°–179° C. (acetonitrile), yield: 47%
4/2: N-(trans-4-nitroxycyclohexylmethyl)-succinic acid monoamide from trans-4-nitroxycyclohexylmethylamine and succinic acid anhydride melting point: 79°–81° C. (ether), yield: 80%.

EXAMPLE 5

N-(trans-4-nitroxycyclohexyl)-succinic acid diamide

A suspension of 3.9 g (0.015 mol) N-(trans-4-nitroxycyclohexyl)-succinic acid monoamide (Example 4) in 100 ml abs. methylene chloride are mixed with 3.1 g (0.015 mol) phosphorus pentachloride, with cooling at 5°-10° C. After 2 h stirring at room temperature, it is distilled off in a vacuum at max. 20° C., triturated with abs. ether and filtered off with suction. The acid chloride is immediately introduced solid into 50 ml 10% ammonia at 5°-10° C. and stirred overnight at room temperature. After suction filtration, there remain 1.2 g of the title compound of the m p 167°-169° C., i.e. 30% of theory.

Analogously, there are obtained:

5/1: N-(trans-4-nitroxycyclohexyl)-maleic acid diamide from N- (trans-4-nitroxycyclohexyl) -maleic acid monoamide (Example 4/1) and ammonia melting point: 151°-152° C. (ethyl acetate), yield: 31%

5/2: N-(trans-4-nitroxycyclohexyl)-N',N'-dimethyl-succinic acid diamide from N-(trans-4-nitroxycyclohexyl)-succinic acid monoamide (Example 4) and dimethylamine melting point: 120°-122° C. (ether), yield: 42%

5/3: N-(trans-4-nitroxycyclohexylmethyl)-succinic acid diamide from N-(trans-4-nitroxycyclohexylmethyl)-succinic acid monoamide and ammonia melting point: 156°-157° C. (ethyl acetate), yield: 63%

5/4: N-(trans-4-nitroxycyclohexylmethyl)-N',N'-dimethylsuccinic acid diamide from N-(trans-4-nitroxycyclohexylmethyl)-succinic acid monoamide and dimethylamine melting point: 70°-71° C. (ether), yield: 40%

EXAMPLE 6 trans-N-propionyl-4-nitroxycyclohexylamine

To a solution of 3.2 g (0.02 mol) trans-4-nitroxycyclohexylamine in 80 ml abs. methylene chloride are added at 5°-10° C. 3 ml (0.02 mol) triethylamine and subsequently 2 g (0.02 mol) propionyl chloride in 20 ml abs. methylene chloride added dropwise thereto. One leaves to stir overnight at room temperature, shakes out 3× with 25 ml of water, dries the organic phase with sodium sulphate and distill off in a vacuum. The residue is triturated with ether and filtered off with suction. There remain 2.8 g of the title compound of the melting point 138°-140° C., i.e. 65% of theory.

Analogously, there are obtained:

6/1: 2-methoxy-N-(trans-nitroxycyclohexyl)-acetic acid amide from trans-4-nitroxycyclohexylamine and methoxyacetic acid chloride melting point: 98°-99° C. (ether), yield: 40%

6/2: 2-acetoxy-N-(trans-4-nitroxycyclohexyl)-acetic acid amide from trans-4-nitroxycyclohexylamine and acetoxyacetic acid chloride melting point: 98°-99° C. (ether), yield: 90%

6/3: 2-acetoxy-N-(trans-4-nitroxycyclohexyl)-propionic acid amide from trans-4-nitroxycyclohexylamine and 2-acetoxypropionic acid chloride melting point: 104°-105° C. (ethyl acetate/ether), yield: 80%

6/4: 3-acetoxy-N-(trans-4-nitroxycyclohexyl)-2,2-dimethylpropionic acid amide from trans-4-nitroxycyclohexylamine and 3-acetoxy-2,2-dimethylpropionic acid chloride melting point: oil, yield: 80%

6/5: N-(trans-4-nitroxycyclohexyl)-nicotinic acid amide from trans-4-nitroxycyclohexylamine and nicotinic acid azide melting point: 171°-173° C. (ethyl acetate), yield: 46%

6/6: N-(trans-4-nitroxycyclohexyl)-isonicotinic acid amide from trans-4-nitroxycyclohexylamine and isonicotinic acid azide melting point: 170°-172° C. (2-propanol), yield: 40%

6/7: 2-acetoxy-N-(trans-4-nitroxycyclohexylmethyl)acetic acid amide from trans-4-nitroxycyclohexylmethylamine and acetoxyacetic acid chloride melting point: 65°-66° C. (ether), yield: 60%

6/8: N-trans-4-nitroxycyclohexyl-2,2-dimethylpropionic acid amide from trans-4-nitroxycyclohexylamine and 2,2-dimethylpropionic acid chloride melting point: 148°-151° C. (ether), yield: 25% of theory 6/9: N-trans-4-nitroxycyclohexylmethanesulphonic acid amide from trans-4-nitroxycyclohexylamine and methanesulphonic acid chloride melting point: 154°-155° C. (ether), yield: 84% of theory 6/10: 2,2-bis-(acetoxymethyl)-N-trans-4-nitroxycyclohexylpropionic acid amide from trans-4-nitroxycyclohexylamine and 2,2-bis(acetoxymethyl)-propionic acid chloride melting point: 95°-97° C. (ethyl acetate), yield 40% of theory 6/11: N-ethoxycarbonyl-trans-4-nitroxycyclohexylamine from trans-4-nitroxycyclohexylamine and chloroformic acid ethyl ester melting point: 93°-94° C. (ether/isohexane), yield: 56% of theory 6/12: 2-acetylmercapto-N-(trans-4-nitroxycyclohexyl)acetic acid amide from trans-4-nitroxycyclohexylamine and 2-acetylmercaptoacetic acid chloride melting point: 127°-129° C. (ether), yield: 67% of theory.

EXAMPLE 7 trans-4-nitroxycyclohexanecarboxylic acid N-(2-methyl-3-butyl-2-yl)-amide 6.2 g (0.075 mol) 2-methyl-3-butyl-2-ylamine are dissolved in 100 ml abs. ethyl acetate and, with cooling at 5°-10° C., 5.2 g (0.025 mol) trans-4-nitroxycyclohexanecarboxylic acid chloride in 25 ml abs. ethyl acetate added dropwise thereto. After 3 h stirring at room temperature, it is shaken out with 100 ml of water, the ethyl acetate phase is dried with sodium sulphate and distilled off in a vacuum. The residue is mixed with ether and filtered off with suction. There remain 2.6 g of the title compound of the melting point 138°-139° C., i.e. 40% of theory.

Analogously, there are obtained:

7/1: trans-4-nitroxycyclohexanecarboxylic acid N-(2-hydroxyethyl)-amide from trans-4-nitroxycyclohexanecarboxylic acid chloride and 2-hydroxyethylamine melting point: 132°-133° C. (ether), yield: 25%

7/2: trans-4-nitroxycyclohexanecarboxylic acid N-(3-hydroxypropyl)-amide from trans-4-nitroxycyclohexanecarboxylic acid chloride and 3-hydroxypropylamine melting point: 78°-79° C. (ether), yield 45%

7/3: trans-4-nitroxycyclohexanecarboxylic acid N-(N,N-dimethylacetamido)-amide from trans-4-nitroxycyclohexanecarboxylic acid chloride and aminoacetic acid acid N,N-dimethylamide melting point: 142°-144° C. (ethanol), yield: 20%

7/4: trans-4-nitroxycyclohexanecarboxylic acid N-(2,2-dimethylacetamido)-amide from trans-4-nitroxycyclohexanecarboxylic acid chloride and 2-amino-2-methylpropionic acid amide melting point: 180°-181° C. (water), yield: 53%

7/5: trans-4-nitroxycyclohexanecarboxylic acid N-(methyl)-hydroxylamide from trans-4-nitroxycyclohexanecarboxylic acid chloride and N-methylhydroxylamine melting point: 125°–126° C.(ether), yield: 53%

7/6: trans-4-nitroxycyclohexanecarboxylic acid N-2-(2-methyl-3-ethyl)-amide from trans-4-nitroxycyclohexanecarboxylic acid chloride and 2-amino-2-methylpropanol melting point: 150°–151° C. (ether), yield: 65% of theory 7/7: trans-4-nitroxycyclohexanecarboxylic acid N-bis-(2-hydroxyethyl)-amide from trans-4-nitroxycyclohexanecarboxylic acid chloride and bis-(2-hydroxyethyl)-amine melting point: 78°–79° C. (ethyl acetate/ether), yield: 80% of theory.

EXAMPLE 8 trans-4-nitroxycyclohexanecarboxylic acid N-(acetic acid) amide 1.1 g (0.015 mol) aminoacetic acid are dissolved in 25 ml of water and 0.6 g (0.015 mol) sodium hydroxide added thereto. After cooling to about 5° C., a solution of 3.1 g (0.015 mol) trans-4-nitroxycyclohexanecarboxic acid chloride in 10 ml dioxane is added dropwise thereto and the pH value is kept at about 12 by the simultaneous addition of 2N sodium hydroxide solution (about 7.5 ml). One leaves to stir for 2 h at room temperature, adjusts the pH value of the reaction mixture to 1 and extracts with ethyl acetate. The organic phase is dried with sodium sulphate and distilled off in a vacuum. After trituration with ether and suction filtration, there remain 1.4 g of the title compound of the melting point 143°–144° C., i.e. 38% of theory.

In analogous manner are obtained:

8/1: trans-4-nitroxycyclohexanecarboxylic acid N-(2-propionic acid) amide from trans-4-nitroxycyclohexanecarboxylic acid chloride and 2-aminopropionic acid melting point: 113°–114° C. (ether), yield: 25%

8/2: trans-4-nitroxycyclohexanecarboxylic acid N-(acetamido) amide from trans-4-nitroxycyclohexanecarboxylic acid chloride and aminoacetic acid amide melting point: 170° C. (ethyl acetate), yield: 35%

EXAMPLE 9

2-Hydroxy-N-(trans-4-nitroxycyclohexyl)-acetic acid amide 6.1 g (0.023 mol) 2-acetoxy-N-(trans-4-nitroxycyclohexyl)-acetic acid amide (Example 6/2) are dissolved in 100 ml of about 5N methanolic ammonia and stirred overnight at room temperature. After distilling off in a vacuum, it is dissolved in ethyl acetate and shaken out with water. The ethyl acetate phase is dried with sodium sulphate and distilled off in a vacuum. The residue is triturated with ether and filtered off with suction. There remain 1.8 g of the title compound of the melting point 81°–83° C., i.e. 36% of theory.

Analogously, there are obtained:

9/1: 2-hydroxy-N-(trans-4-nitroxycyclohexyl)-propionic acid amide from 2-acetoxy-N-(trans-4-nitroxycyclohexyl)propionic acid amide (Example 6/3) melting point: 117°–118° C. (ether), yield: 23%

9/2: 2-hydroxy-N-(trans-4-nitroxycyclohexyl)-2,2-dimethylpropionic acid amide from 2-acetoxy-N-(trans-4-nitroxycyclohexyl)-2,2-dimethylpropionic acid amide (Example 6/4) melting point: 100°–101° C. (ether), yield 28%

9/3: 2-hydroxy-N-(trans-4-nitroxycyclohexylmethyl)acetic acid amide from 2-acetoxy-N-(trans-4-nitroxycyclohexylmethyl)acetic acid amide (Example 6/7) melting point: 111°–112° C. (ether), yield: 74%

9/4: 2,2-bis-(hydroxymethyl)-N-trans-4-nitroxycyclohexylpropionic acid amide from 2,2-bis-(acetoxymethyl)-N-trans-4-nitroxycyclohexylpropionic acid melting point: 110°–112° C. (ethyl acetate), yield: 20% of theory.

EXAMPLE 10

4-Hydroxy-N-(trans-4-nitroxycyclohexyl)-butyric acid amide 4.8 g (0.03 mol) trans-4-nitroxycyclohexylamine are mixed with 5.7 ml 4-butyrolactone and stirred for 3 d at room temperature. For the removal of the excess lactone, it is filtered over a silicic gel acid with ethyl acetate. After collection of the pure fractions, it is distilled in a vacuum, triturated with ether and filtered off with suction. There remain 2.1 g of the title compound of the melting point 58°–60° C., i.e. 28% of theory.

EXAMPLE 11

N-(trans-4-nitroxycyclohexyl)-(S)-Pyroglutamic acid amide 2.1 g (0.016 mol) (S)-pyroglutamic acid (2-pyrrolidinone-5-carboxylic acid) are dissolved in 50 ml abs. tetrahydrofuran and 2.5 ml (0.018 mol) triethylamine. With cooling to about 5° C., 2 ml (0.016 mol) pivaloyl chloride in 10 ml abs. tetrahydrofuran are added dropwise thereto. After 15 min stirring at 5° C., one adds dropwise thereto a solution of 3.9 g trans-4-nitroxycyclohexylamine in 40 ml abs. tetrahydrofuran and 2.8 ml (0.02 mol) triethylamine. Thereafter, one allows to stir for 2 d at room temperature, filters off with suction and removes the solvent in a vacuum. The residue is dissolved in ethyl acetate and shaken out with sodium hydrogen carbonate. After drying of the ethyl acetate phase with sodium sulphate, distilling off in a vacuum, trituration with ether and suction filtration, there remain 1.5 g of the title compound of the melting point 166° C., i.e. 35% of theory.

EXAMPLE 12

N-(trans-4-nitroxycyclohexyl)-nicotinic acid amide N-oxide 1.5 g (0.005 mol) N-(trans-4-nitroxycyclohexyl)nicotinic acid amide (Example 6/5) are dissolved in 4 ml acetic acid, 4 ml 30% hydrogen peroxide added thereto and stirred for 2 d at 40° C. After concentration and trituration with ethyl acetate, the crystals awe filtered off with suction. There remain 0.9 g of the title compound of the melting point 170°–171° C., i.e. 53% of theory.

One obtains analogously:

12/1: N-(trans-4-nitroxycyclohexyl)-isonicotinic acid amide N-oxide from N-(trans-4-nitroxycyclohexyl)-isonicotinic acid amide (Example 6/6) melting point: 180° C. (ethyl acetate), yield: 82%.

EXAMPLE 13 trans-4-Hydroxycyclohexylmethylamine (VII)

a) cis-trans-4-hydroxycyclohexanecarboxylic acid 184 g (1.07 mol) cis-trans-4-hydroxycyclohexanecarboxylic acid ether ester (lit.: JACS 70, (1948) 1898) are heated to reflux in 1.8 l of water with 119.8 g (2.14 mol)

potassium hydroxide for 3 h. After acidification with conc. hydrochloric acid and extraction with methylene chloride, there are obtained 146 g of acid of the m.p. 111°-115° C., i.e. 94% of theory.

b) trans-4-O-acetylcyclohexanecarboxylic acid 145 g (1.01 mol) cis-trans-4-hydroxycyclohexanecarboxylic acid are suspended in 1 l acetic acid, 123.5 g (1.21 mol) acetyl chloride added dropwise thereto and thereupon heated to reflux for 5 h. After distilling off of the acetic acid, about 200 ml of water are added thereto and distilled to dryness. The residue is taken up in diisopropyl ether and, after crystallisation, filtered off with suction. There remain 112 g of crude product. After recrystallisation from 740 ml of water, these are obtained 84 g, i.e 44% of theory, of pure trans compound of the m.p. 140°-141° C.

c) trans-4-O-acetylcyclohexanecarboxylic acid methyl ester 84 g (0.45 mol) trans-4-O-acetylcyclohexanecarboxylic acid are dissolved in 1 l methanol, 8.6 g (0.045 mol) p-toluenesulphonic acid added thereto and heated under reflux for about 20 h. After distilling off of the methanol, the residue is dissolved in water and neutralised with sodium hydrogen carbonate. One saturates the aqueous solution with common salt and extracts several times with ethyl acetate. The ethyl acetate extracts are dried with sodium sulphate, filtered off and distilled off There remain 72.7 g of ester, i.e. 80% of theory, as colourless oil.

d) trans-4-hydroxycyclohexanecarboxylic acid amide 36 g (0.18 mol) trans-4-O-acetylcyclohexanecarboxylic acid methyl ester are heated for 24 h to 100° C. in a 2 l shaking autoclave in 500 ml methanol and 500 ml liquid ammonia. After evaporation of the ammonia and distilling off of the methanol, the residue is triturated with ether and filtered off with suction. There remain 21.6 g of amide of the m.p. 208°-210° C., i.e. 83% of theory.

e) trans-4-hydroxycyclohexylmethylamine

To a suspension of 11.4 g (0.3 mol) lithium aluminum hydride in 500 ml anhydrous tetrahydrofuran are introduced 21.6 g (0 15 mol) solid trans-4-hydroxycyclohexanecarboxylic acid amide and heated under reflux for 24 h. After decomposition with 45 ml saturated common salt solution, it is filtered off with suction and the filtrate distilled The residue is triturated with ether and the crystals filtered off with suction. There remain 11 g of amine, i.e. 57% of theory, of the m.p. 137°-139° C.

EXAMPLE 14

Pharmacological investigations a) Object of investigation

It was the object of the present investigations to find nitrates, the action of which continues longer and which therapeutically permit the expectation that a single daily administration suffices for the therapeutic use. Quite apart from the fact that a single daily administration instead of a multiple one signifies an improvement for the compliance of the patient, in this way the pharmacokinetic action profile of a substance can be substantially influenced, i.e. one may start from the view that the difference between maximum and minimum level is clearly more favourable because of the smaller concentration decrease of the substance level.

b) Method

For the detection of the denitration, which represents the action principle of all nitrates, there was evaluated the speed of denitration in relation to the known ISDN metabolite IS-5MN. For this purpose, rats were sacrificed under narcosis and the liver reperfused with a correspondingly concentrated equimolar $(5 \times 10^{-5} M/l)$ solution of IS-5-MN or the substances to be tested, in each case for 4 min, and the liberated amount of $NO_2$ determined in the perfusate. In order to have comparable conditions, the perfusion with IS-5-MN (standard substance) as control was so administered three times as were the third perfusion an unknown substance (in this way, a liver capability changed under the experimental conditions can be recognised and correspondingly taken into account). The $V_{rel}$ values (relative speed of denitration), third column in the Table, indicate how high the speed of denitration is in comparison with IS-5-MN High values signify rapid denitration, lower values slow denitration.

c) Results

With regard to the speed of denitration through the perfused rat liver, in comparison with isosorbitol 5-mononitrate (IS-5-MN) with $V_{rel}=0.95$ the investigated compounds are better, i.e. smaller values of the speed of denitration are found than in the case of IS- 5-MN.

TABLE

| Example No. | $V_{rel}$ |
|---|---|
| 1 | 0.45 |
| 5/3 | 0.49 |
| 7/7 | 0.49 |
| 10 | 0.28 |
| 12/1 | 0.36. |

We claim:

1. Cyclohexanol nitrates of the formula I

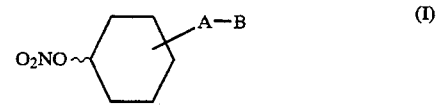

wherein A is a valency bond or a $C_1$-$C_6$ alkylene chain; and wherein B is the group —$NR^1$—CO—Z, —$NR^1$—$SO_2$—Z, or —CO—$NR^2$—Z, wherein $R^1$ is hydrogen or a $C_1$-$C_6$ alkyl group;

$R^2$ is hydrogen, hydroxyl, hydroxy —$C_1$-$C_6$ alkyl, $C_1$-$C_6$ alkoxy, $C_1$-$C_6$ alkyl, $C_2$-$C_6$ alkenyl, or $C_2$-$C_6$ alkynol;

Z is hydrogen, an unsubstituted or substituted $C_1$-$C_6$ alkyl, $C_2$-$C_6$ alkenyl, or $C_2$-$C_6$ alkynyl group wherein the substituents are at least one of hydroxyl, $C_1$-$C_6$ alkylcarbonyloxy, $C_1$-$C_6$ alkoxy, halogen, cyano, carboxyl, $C_1$-$C_6$ alkoxycarbonyl, —CO—$NR^3R^4$, mercapto, $C_1$-$C_6$ alkylmercapto or $C_1$-$C_6$ alkylcarbonylmercapto, or Z is a $C_3$-$C_6$ cycloalkyl group, and for the case that B is an $NR^1$—CO—Z group, Z can also be $C_1$-$C_6$ alkoxy; and $R^3$ and $R^4$ can be the same or different, and, in each case independently of one another, signify hydrogen or a $C_1$-$C_6$ alkyl group, as well as their optically active forms and physiologically compatible salts.

2. Cyclohexanol nitrates according to claim 1 wherein A is a valency bond or a $C_1$-$C_3$ alkylene group.

3. Cyclohexanol nitrates according to claim 2 wherein A is $CH_2$.

4. Cyclohexanol nitrates according to claim 1 wherein $R^1$ is a hydrogen atom or a $C_1$-$C_3$ alkyl group.

5. Cyclohexanol nitrates according to claim 4 wherein $R^1$ is $CH_3$ or $-C_2H_5$.

6. Cyclohexanol nitrates according to claim 1 wherein $R^2$ is a hydrogen atom, hydroxyl, hydroxy $-C_1$-$C_3$ alkyl or $C_1$-$C_3$ alkyl.

7. Cyclohexanol nitrates according to claim 6 wherein $R^2$ is $-CH_3$ or $-C_2H_5$.

8. Cyclohexanol nitrates according to claim 1 wherein $R^3$ and $R^4$ are, independently, hydrogen or a $C_1$-$C_3$ alkyl.

9. Cyclohexanol nitrates according to claim 8 wherein $R^3$ and $R^4$ are $-CH_3$.

10. Cyclohexanol nitrates according to claim 1 wherein Z is a hydrogen atom, a $C_1$-$C_6$ alkyl, $C_2$-$C_6$ alkenyl, or a $C_2$-$C_6$ alkynyl, wherein the alkyl and alkenyl groups can be substituted once by halogen, a carboxyl, a carboxamido, $C_1$-$C_3$ alkoxy, $C_1$-$C_3$ alkylcarbonyloxy, hydroxyl, or a cyano group, or said alkyl or alkenyl groups can be substituted twice by hydroxyl or $C_1$-$C_3$ alkylcarbonyloxy groups.

11. Cyclohexanol nitrates according to claim 1 selected from the group consisting of: trans-N-acetyl-4-nitroxycyclohexylamine, N-(trans-4-nitroxycyclohexylmethyl) succinic acid diamide, trans-4-nitroxycyclohexanecarboxylic acid N-bis-(2-hydroxyethyl)-amide, 4-hydroxy-N-(trans-4-nitroxycyclohexyl) butyric acid amide.

12. A pharmaceutical composition for producing a nitrate like effect comprising an effective amount of a cyclohexanol nitrate of claim 1 and a pharmaceutically acceptable carrier and/or adjuvant.

13. A method of producing a nitrate-like effect in a patient in need of such effect, comprising administering to the patient a therapeutically effective amount of the compound of claim 1.

14. A compound of formula II

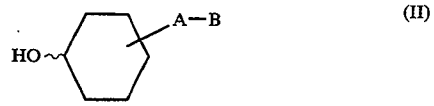

wherein A is a valency bond or a $C_1$-$C_6$ alkylene chain; and wherein B is the group $-NR^1-CO-Z$, $-NR^1-SO_2-Z$, or $-CO-NR^2-Z$, wherein $R^1$ is hydrogen or a $C_1$-$C_6$ alkyl group;

$R^2$ is hydrogen, hydroxyl, hydroxy $-C_1$-$C_6$ alkyl, $C_1$-$C_6$ alkoxy, $C_1$-$C_6$ alkyl, $C_2$-$C_6$ alkenyl, or $C_2$-$C_6$ alkynol;

Z is an unsubstituted or substituted $C_1$-$C_6$ alkyl, $C_2$-$C_6$ alkenyl, or $C_2$-$C_6$ alkynyl group wherein the substituents are at least one of hydroxyl, $C_1$-$C_6$ alkylcarbonyloxy, $C_1$-$C_6$ alkoxy, cyano, carboxyl, $C_1$-$C_6$ alkoxycarbonyl, $-CO-NR^3R^4$, mercapto, $C_1$-$C_6$ alkylmercapto or $C_1$-$C_6$ alkylcarbonylmercapto; and $R^3$ and $R^4$ can be the same or different, and, in each case independently of one another, signify hydrogen or a $C_1$-$C_6$ alkyl group.

15. A compound according to claim 14 selected from the group consisting of:

trans-4-hydroxycyclohexanecarboxylic acid amide, and trans-N-Acetyl-4-hydroxycyclohexylamine.

* * * * *

UNITED STATES PATENT AND TRADEMARK OFFICE
CERTIFICATE OF CORRECTION

PATENT NO. : 5,411,989
DATED : May 2, 1995
INVENTOR(S) : Michel, et. al.

It is certified that error appears in the above-indentified patent and that said Letters Patent is hereby corrected as shown below:

```
Title page;

[62] line 2, add -- , which is a 371 of
         PCT/EP91/00290, Feb. 14, 1991 --.

[30] add line 3,
         - Feb. 14, 1991 [GB] PCT..........PCT/EP91/00290 --
```

Signed and Sealed this

Twelfth Day of March, 1996

Attest:

BRUCE LEHMAN

*Attesting Officer*        *Commissioner of Patents and Trademarks*